(12) United States Patent
Heindl et al.

(10) Patent No.: US 12,203,905 B2
(45) Date of Patent: Jan. 21, 2025

(54) METHOD FOR IDENTIFYING A REAGENT DURING A PROCESS IN AN ANALYSIS SYSTEM

(71) Applicant: Roche Diagnostics Operations, Inc., Indianapolis, IN (US)

(72) Inventors: Dieter Heindl, Munich (DE); Uwe Kobold, Weilheim (DE); Christoph Seidel, Weilheim (DE); Martin Rempt, Penzberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 16/438,775

(22) Filed: Jun. 12, 2019

(65) Prior Publication Data

US 2019/0293611 A1 Sep. 26, 2019

Related U.S. Application Data

(63) Continuation of application No. PCT/EP2017/084012, filed on Dec. 21, 2017.

(30) Foreign Application Priority Data

Dec. 23, 2016 (EP) .................................. 16206598

(51) Int. Cl.
*G01N 30/08* (2006.01)
*G01N 30/02* (2006.01)
(Continued)

(52) U.S. Cl.
CPC ............. *G01N 30/08* (2013.01); *G01N 30/06* (2013.01); *G01N 30/28* (2013.01); *G01N 30/466* (2013.01);
(Continued)

(58) Field of Classification Search
CPC ............... G01N 30/02; G01N 33/6848; G01N 2030/027; G01N 30/06; G01N 30/28;
(Continued)

(56) References Cited

U.S. PATENT DOCUMENTS 5,677,186 A 10/1997 Anderson et al.
5,882,933 A 3/1999 Li et al.
(Continued)

FOREIGN PATENT DOCUMENTS

CN 1427953 A 7/2003
CN 1873409 A 12/2006
(Continued)

OTHER PUBLICATIONS

International Search Report issued Mar. 26, 2018, in Application No. PCT/EP2017/084012, 2 pp.
(Continued)

*Primary Examiner* — Jennifer Wecker
*Assistant Examiner* — Bryan Kilpatrick
(74) *Attorney, Agent, or Firm* — Taft Stettinius & Hollister LLP

(57) ABSTRACT

A method for identifying a reagent during a process in an analysis system is disclosed. The analysis system comprises a liquid chromatograph and a mass spectrometer. The method comprises providing a reagent, adding at least one chemical substance to the reagent with a concentration being below a detection level of the mass spectrometer, enriching the chemical substance within the liquid chromatograph to a concentration above the detection level of the mass spectrometer, processing the reagent together with the enriched chemical substance by means of the analysis system, and identifying the reagent based on a detection of a substance detection signal of the mass spectrometer representing the chemical substance.

14 Claims, 2 Drawing Sheets

(51) Int. Cl.
*G01N 30/06* (2006.01)
*G01N 30/28* (2006.01)
*G01N 30/46* (2006.01)
*G01N 30/72* (2006.01)
*G01N 33/58* (2006.01)
*G01N 33/68* (2006.01)
*B01D 15/34* (2006.01)
*B01D 59/44* (2006.01)
*H01J 49/06* (2006.01)
*H01J 49/10* (2006.01)

(52) U.S. Cl.
CPC ......... *G01N 30/7233* (2013.01); *G01N 33/58* (2013.01); *G01N 33/6848* (2013.01); *B01D 15/34* (2013.01); *B01D 59/44* (2013.01); *G01N 2030/027* (2013.01); *H01J 49/063* (2013.01); *H01J 49/10* (2013.01)

(58) Field of Classification Search
CPC ...... G01N 30/08; G01N 30/72; C12Q 1/6872; B01D 15/34; B01D 59/44; H01J 49/063; H01J 49/10
See application file for complete search history.

(56) References Cited

U.S. PATENT DOCUMENTS

| | | | |
|---|---|---|---|
| 6,147,344 A | 11/2000 | Annis et al. | |
| 6,641,783 B1 | 11/2003 | Pidgeon et al. | |
| 7,160,735 B2 | 1/2007 | Dehlinger et al. | |
| 7,498,568 B2 | 3/2009 | Overney et al. | |
| 7,815,803 B2* | 10/2010 | Kobold | B01D 15/325 |
| | | | 210/198.2 |
| 7,816,304 B2 | 10/2010 | Schmidt et al. | |
| 7,820,023 B2 | 10/2010 | Curcio | |
| 7,868,547 B2 | 1/2011 | Pappin et al. | |
| 7,906,341 B2 | 3/2011 | Purkayastha et al. | |
| 8,829,429 B2 | 9/2014 | Geyer et al. | |
| 8,940,546 B2 | 1/2015 | Grothe, Jr. et al. | |
| 8,945,940 B2 | 2/2015 | Shin et al. | |
| 10,088,460 B2 | 10/2018 | DeWitte et al. | |
| 10,488,374 B2 | 11/2019 | Hanafusa et al. | |
| 12,031,962 B2* | 7/2024 | Heindl | G01N 30/7233 |
| 2003/0194717 A1 | 10/2003 | Schmidt et al. | |
| 2004/0033625 A1 | 2/2004 | Achersold | |
| 2004/0072250 A1 | 4/2004 | Baranov et al. | |
| 2005/0208550 A1 | 9/2005 | Pappin et al. | |
| 2006/0160131 A1 | 7/2006 | Vandekerchove et al. | |
| 2006/0186028 A1 | 8/2006 | Hughes | |
| 2009/0090855 A1 | 4/2009 | Kobold et al. | |
| 2009/0090856 A1 | 4/2009 | Grant et al. | |
| 2010/0003762 A1 | 1/2010 | Kolbe et al. | |
| 2010/0068819 A1 | 3/2010 | Hoffmann | |
| 2011/0028330 A1 | 2/2011 | Hoffmann et al. | |
| 2012/0269728 A1 | 10/2012 | Jen et al. | |
| 2013/0102478 A1 | 4/2013 | Amoura | |
| 2014/0093968 A1 | 4/2014 | Grothe, Jr. et al. | |
| 2014/0158881 A1 | 6/2014 | Cooper | |
| 2014/0349885 A1 | 11/2014 | Dey et al. | |
| 2016/0139140 A1 | 5/2016 | Thompson et al. | |
| 2016/0169902 A1 | 6/2016 | Grothe, Jr. et al. | |

FOREIGN PATENT DOCUMENTS

| | | |
|---|---|---|
| CN | 101358969 A | 2/2009 |
| CN | 101421609 A | 4/2009 |
| CN | 101542291 A | 9/2009 |
| CN | 101848886 A | 9/2010 |
| CN | 102099685 A | 6/2011 |
| CN | 102484030 A | 5/2012 |
| CN | 103370616 A | 10/2013 |
| CN | 104508487 A | 4/2015 |
| CN | 105209921 A | 12/2015 |
| CN | 105699478 A | 6/2016 |
| EP | 1718962 B1 | 4/2006 |
| EP | 1705482 A2 | 9/2006 |
| EP | 1918714 A1 | 5/2008 |
| EP | 2108957 A1 | 10/2009 |
| GB | 2430740 A | 4/2007 |
| JP | H07503541 A | 4/1995 |
| JP | 2002527756 A | 8/2002 |
| JP | 2003529059 A | 9/2003 |
| JP | 2005538369 A | 12/2005 |
| JP | 2010507785 A | 10/2007 |
| JP | 2010509567 A | 3/2010 |
| JP | 2010156706 A | 7/2010 |
| JP | 2010249838 A | 11/2010 |
| JP | 2011504596 | 2/2011 |
| JP | 2011519021 A | 6/2011 |
| JP | 2012159356 A | 8/2012 |
| JP | 2013088215 B2 | 5/2013 |
| JP | 2014221705 A | 11/2014 |
| JP | 2015503753 A | 2/2015 |
| JP | 2015055531 A | 3/2015 |
| WO | 200064557 A1 | 11/2000 |
| WO | 0229414 A3 | 4/2002 |
| WO | 2007087534 A2 | 8/2007 |
| WO | 2008005846 A2 | 1/2008 |
| WO | 2009091933 A2 | 7/2009 |
| WO | 2009125316 A2 | 10/2009 |
| WO | 2016035139 A1 | 10/2016 |

OTHER PUBLICATIONS

Gygi et al., Quantitative analysis of complex protein mixtures using isotope-coded affinity tags; Nature Biotechnology,, Oct. 1999, vol. 17, pp. 994-999.

* cited by examiner

METHOD FOR IDENTIFYING A REAGENT DURING A PROCESS IN AN ANALYSIS SYSTEM

CROSS-REFERENCE TO RELATED APPLICATIONS

This application is a continuation of International Patent Application No. PCT/EP2017/084012, filed 21 Dec. 2017, which claims the benefit of European Patent Application No. 16206598.1, filed 23 Dec. 2016, the disclosures of which are hereby incorporated herein by reference in their entirety.

TECHNICAL FIELD

The present disclosure relates to a method for identifying a reagent during a process in an analysis system.

BACKGROUND

There is growing interest for the implementation of mass spectrometry and more specifically of liquid chromatography coupled to tandem mass spectrometry (LC-MS/MS) in different types of laboratories such as a clinical laboratory. The number of published methods especially for small molecules in therapeutic drug monitoring or drug of abuse testing is increasing.

Some ready to use kits for pre-validated clinical MS applications are becoming commercially available. The use of mass spectrometry, however, even in connection with such kits, may not be regulatory approved for clinical diagnostics. This is mostly because of lack of standardized procedures, except for a very few analytes, and because of the still large number of user dependent factors, e.g., due to a number of manual steps that are still conducted and the diversity of hardware components that may be used and combined, and that play a role in delivering reliable and reproducible results of clinical relevance. In particular, sample preparation is typically a manual and tedious procedure. Protein precipitation with subsequent centrifugation is the most popular method to remove unwanted and potentially disturbing sample matrix. The use of kits may in part facilitate sample preparation that can be at least in part automated. Kits are however available only for a limited number of analytes of interest and the entire process from sample preparation, to separation and detection remains complex, requiring the attendance of highly trained laboratory personnel to run highly sophisticated instruments.

Also, typically, a batch approach is followed, where a batch of samples prepared in advance under the same preparation conditions undergo consecutive separation runs under the same separation conditions. This approach however does not enable high throughput and is not flexible, e.g., does not allow re-scheduling (changing a pre-defined processing sequence) in view for example of incoming emergency samples that have higher priority and have to be processed first.

The implementation of liquid chromatography coupled to tandem mass spectrometry allows to process several samples in parallel. The samples usually have to be prepared before being processed through the LC-MS-system. For this purpose, different types of reagents are used. At least one of these reagents is added to the sample for preparation thereof. Ensuring reagent identity and quality is an essential feature in automated systems for mass spectrometric analysis. Currently, it is in the responsibility of the user to ensure that the correct reagents are loaded onto the system, including identity and quality of the reagents and correct connection to the different flow paths. Currently there is no automated direct control available by the system. Further, ensuring flow path integrity is an essential feature in highly parallelized LC systems for mass spectrometric analysis. Currently this is ensured only by timing and positioning of flow diverting valves.

BRIEF SUMMARY

It is against the above background that the embodiments of the present disclosure provide certain unobvious advantages and advancements over the prior art. In particular, the inventors have recognized a need for improvements in a method for identifying a reagent during a process in an analysis system, and wherein the analysis system can comprise a liquid chromatograph and a mass spectrometer.

Although the embodiments of the present disclosure are not limited to specific advantages or functionality, it is noted that the present disclosure aims to provide an automated direct control of the reagent in an analysis system using liquid chromatography coupled to mass spectrometry by the mass spectrometer itself. Thus, the disclosed embodiments aim to provide a convenient and reliable method which, therefore, is suitable for specific analytical methods such as clinical diagnostics. In particular, high-throughput, e.g., up to 100 samples/hour or more with random access sample preparation and LC separation can be obtained while the respective reagents may be identified throughout the complete process. Moreover, the method can be fully automated increasing the walk-away time and decreasing the level of skills required.

In accordance with one embodiment of the present disclosure, a method for identifying a reagent during a process in an analysis system is provided, wherein the analysis system comprises a liquid chromatograph and a mass spectrometer, the method comprising: providing a reagent, adding at least one chemical substance to the reagent with a concentration being below a detection level of the mass spectrometer, enriching the chemical substance within the liquid chromatograph to a concentration above the detection level of the mass spectrometer, processing the reagent together with the enriched chemical substance with the analysis system, and identifying the reagent based on a detection of a substance detection signal of the mass spectrometer representing the chemical substance.

Embodiments of the disclosed method for identifying a reagent during a process in an analysis system have the features of the independent claim. Further embodiments of the disclosure, which may be realized in an isolated way or in any arbitrary combination, are disclosed in the dependent claims.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
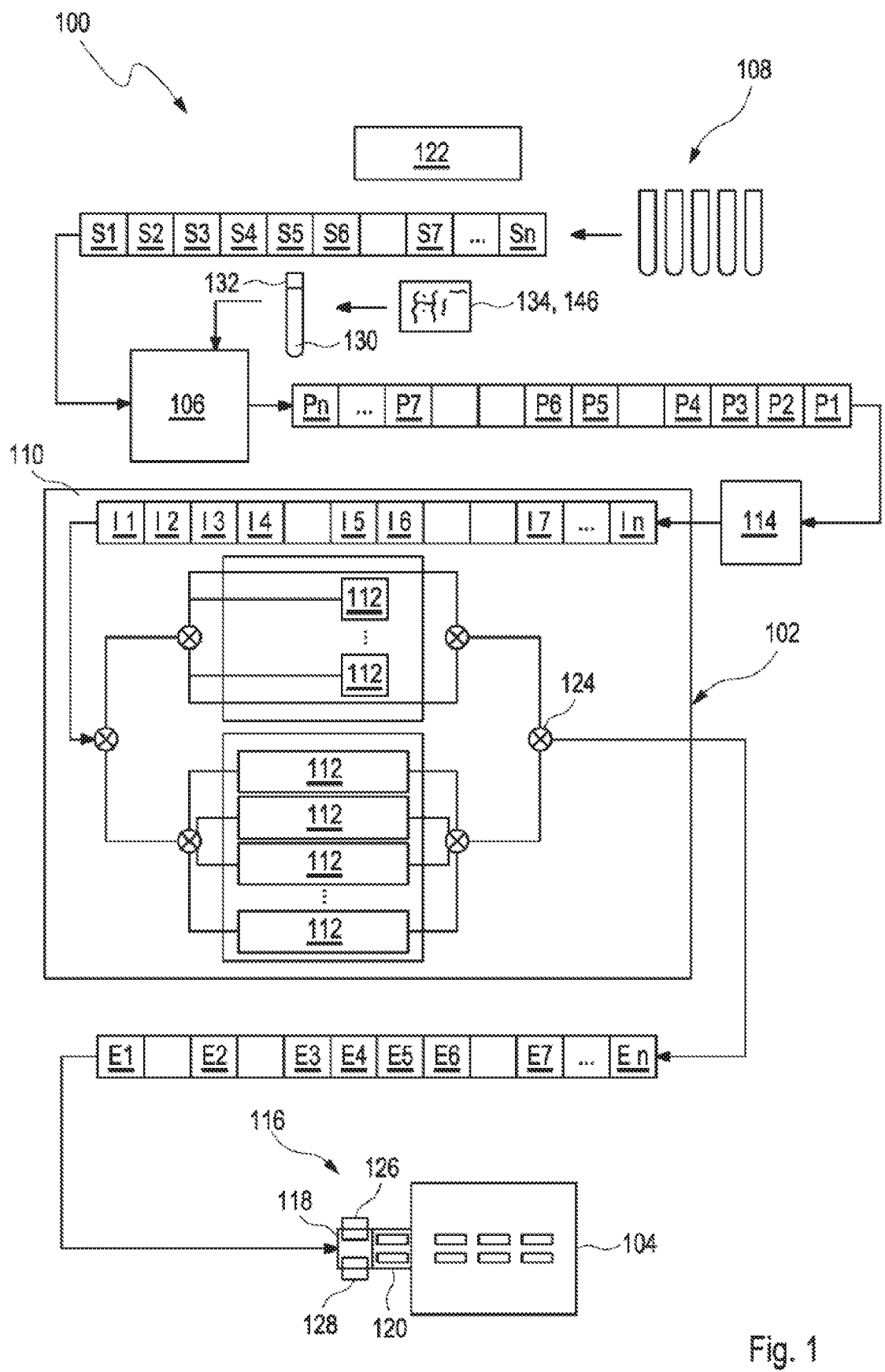
FIG. 1 shows a schematic representation of an analysis system and a method for tracking a sample identity during a process in an analysis system.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically", "typically", "more typically", or similar terms are used in conjunction with additional/alternative features, without restricting alternative possibilities. Thus, features introduced by these terms are additional/alternative features and are not intended to restrict the scope of the claims in any way. The disclosure may, as the skilled person will recognize, be performed by using alternative features. Similarly, features introduced by "in an embodiment of the disclosure" or similar expressions are intended to be additional/alternative features, without any restriction regarding alternative embodiments of the disclosure, without any restrictions regarding the scope of the disclosure, and without any restriction regarding the possibility of combining the features introduced in such way with other additional/alternative or non-additional/alternative features of the disclosure.

According to the disclosed method, a method for identifying a reagent during a process in an analysis system disclosed. The analysis system comprises a liquid chromatograph and a mass spectrometer. The method comprises:
  providing a reagent,
  adding at least one chemical substance to the reagent with a concentration being below a detection level of the mass spectrometer,
  enriching the chemical substance within the liquid chromatograph to a higher concentration above the detection level of the mass spectrometer,
  processing the reagent together with the enriched chemical substance by means of the analysis system, and
  identifying the reagent based on a detection of a substance detection signal of the mass spectrometer representing the chemical substance.

The term "analysis system" as used herein encompasses any system comprising at least a liquid chromatograph and a mass spectrometer configured to obtain a measurement value. An analysis system is operable to determine via various chemical, biological, physical, optical or other technical procedures a parameter value of a sample or a component thereof. An analysis system may be operable to measure said parameter of the sample or of at least one analyte and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analysis system may comprise units assisting with the pipetting, dosing, and mixing of samples and/or reagents. The analysis system may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analysis system may comprise a process and detection system whose workflow is optimized for certain types of analysis. Examples of such analysis systems are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The analysis system may be designed as a clinical diagnostics system or may be part of a clinical diagnostics system.

A "clinical diagnostics system" as used herein refers to a laboratory automated apparatus dedicated to the analysis of samples for in vitro diagnostics. The clinical diagnostics system may have different configurations according to the need and/or according to the desired laboratory workflow. Additional configurations may be obtained by coupling a plurality of apparatuses and/or modules together. A "module" is a work cell, typically smaller in size than the entire clinical diagnostics system, which has a dedicated function. This function can be analytical but can be also pre-analytical or post analytical or it can be an auxiliary function to any of the preanalytical function, analytical function or post-analytical function. In particular, a module can be configured to cooperate with one or more other modules for carrying out dedicated tasks of a sample processing workflow, e.g., by performing one or more pre-analytical and/or analytical and/or post-analytical steps. In particular, the clinical diagnostics system can comprise one or more analytical apparatuses, designed to execute respective workflows that are optimized for certain types of analysis, e.g., clinical chemistry, immunochemistry, coagulation, hematology, liquid chromatography separation, mass spectrometry, etc. Thus the clinical diagnostic system may comprise one analytical apparatus or a combination of any of such analytical apparatuses with respective workflows, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The clinical diagnostics system can comprise functional units such as liquid handling units for pipetting and/or pumping and/or mixing of samples and/or reagents and/or system fluids, and also functional units for sorting, storing, transporting, identifying, separating, and detecting.

The term "sample" as used herein refers to a biological material suspected of containing one or more analytes of interest and whose detection, qualitative and/or quantitative, may be associated to a clinical condition. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The sample can be pretreated prior to use, such as preparing plasma from blood, diluting viscous fluids, lysis or the like; methods of treatment can involve filtration, centrifugation, distillation, concentration, inactivation of interfering components, and the addition of reagents. A sample may be used directly as obtained from the source in some cases or following a pretreatment and/or sample preparation workflow to modify the character of the sample, e.g., after adding an internal standard, after being diluted with another solution or after having being mixed with reagents, e.g., to enable carrying out one or more in vitro diagnostic tests, or for enriching (extracting/separating/concentrating) analytes of interest and/or for removing matrix components potentially interfering with the detection of the analyte(s) of interest. The term "sample" is tendentially used to indicate a sample before sample preparation whereas the term "prepared sample" is used to refer to samples after sample preparation. In non-specified cases the term "sample" may generally indicate either a sample before sample preparation or a sample after sample preparation or both. Examples of analytes of interest are vitamin D, drugs of abuse, therapeutic drugs, hormones, and metabolites in general. The list is however not exhaustive.

The term "liquid chromatograph" as used herein refers to an apparatus configured to be used for liquid chromatography (LC). LC is a separation technique in which the mobile phase is a liquid. It can be carried out either in a column or a plane. Present day liquid chromatography that generally utilizes very small packing particles and a relatively high pressure is referred to as high performance liquid chromatography (HPLC). In HPLC the sample is forced by a liquid at high pressure (the mobile phase) through a column that is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18=octadecylsilyl as the stationary phase) is termed reversed phase liquid chromatography (RPLC).

The term "mass spectrometer" as used herein refers to an apparatus configured to be used for mass spectrometry (MS). MS is an analytical technique that ionizes chemical species and sorts the ions based on their mass to charge ratio. In simpler terms, a mass spectrum measures the masses within a sample. Mass spectrometry is used in many different fields and is applied to pure samples as well as complex mixtures. A mass spectrum is a plot of the ion signal as a function of the mass-to-charge ratio. These spectra are used to determine the elemental or isotopic signature of a sample, the masses of particles and of molecules, and to elucidate the chemical structures of molecules, such as peptides and other chemical compounds. In a typical MS procedure, a sample, which may be solid, liquid, or gas, is ionized, for example by bombarding it with electrons. This may cause some of the sample's molecules to break into charged fragments. These ions are then separated according to their mass-to-charge ratio, typically by accelerating them and subjecting them to an electric or magnetic field: ions of the same mass-to-charge ratio will undergo the same amount of deflection. The ions are detected by a mechanism capable of detecting charged particles, such as an electron multiplier. Results are displayed as spectra of the relative abundance of detected ions as a function of the mass-to-charge ratio. The atoms or molecules in the sample can be identified by correlating known masses to the identified masses or through a characteristic fragmentation pattern.

The term "reagent" as used herein refers to a substance used for treatment of a sample in order to prepare the sample for analysis, to enable a reaction to occur, or to enable detection of a physical parameter of the sample or analyte contained in the sample. In particular, a reagent can be a substance that is or comprises a reactant, typically a compound or agent capable, e.g., of binding to or chemically transforming one or more analytes present in a sample or an unwanted matrix component of the sample. Examples of reactants are enzymes, enzyme substrates, conjugated dyes, protein-binding molecules, ligands, nucleic acid binding molecules, antibodies, chelating agents, promoters, inhibitors, epitopes, antigens, and the like. However, the term reagent is used to include any fluid that can be added to a sample including a dilution liquid, including water or other solvent or a buffer solution, or a substance that is used for disruption of specific or nonspecific binding of an analyte to a protein, binding proteins or surfaces. A sample may be provided for example in sample containers such as sample tubes, including primary tubes and secondary tubes, or multi-well plates, or any other sample carrying support. Reagents may be arranged for example in the form of containers or cassettes containing individual reagents or group of reagents and placed in appropriate receptacles or positions within a storage compartment or conveyor. Other types of reagents or system fluids may be provided in bulk containers or via a line supply.

The term "chemical substances" as used herein refers to any chemical substance being different from the reagent to which the substance is allocated or added. Basic requirement is that the used chemical substance shows almost identical behavior during the reagent processing and chromatography than the reagent of interest as it has to follow the same workflow as the reagent. This could be achieved by using chemical isotopes or substances with similar polarity as the reagent.

With the disclosed method, a possibility for chemical coding is provided. The possibility of chemical coding is a special feature which is made possible by the high multiplexing capabilities of mass spectrometric detection, which enables the detection of additional signals such as background signals at any time during the measurement provided that the concentration of the chemical substance is sufficiently high so as to be above the detection level of the mass spectrometer. For this purpose, the disclosed method suggests to enrich the chemical substance to a concentration above the detection level of the mass spectrometer. The enriching process may be carried out at any arbitrary point of time. As the chemical substance is below the detection level of the mass spectrometer before being enriched, the mass spectrometer will not detect the chemical substance during normal applications. A combination of several markers (present/not present; high/low concentration, etc.) would allow unambiguously labeling of all reagents which are on the system. The chemical substance is spiked into the system reagent(s) during production of the specific reagent lot which are mainly HPLC eluents like water, acetonitrile, methanol and the like. The chemical substance is present in the LC-MS system background signals at any time during the analysis. Thus, the identity of the specific reagent lot can be traced back during any sample analysis to the production event and manufacturer.

As it is likely that the chemical substances are present as minor, trace components in the system regents (solvents) and will be continuously infused into the analytical system such as HPLC column, trapping column, mass spectrometric ion source and the like, any unrequested enrichment of these trace components has to be avoided as this could affect the analysis system. Thus for tracking purpose the used chemicals should have specific elution and detection behavior, depending on the used chromatographic conditions.

With the disclosed method, the chemical substance(s) is (are) present in the solvent in concentrations levels which may be easily detected by mass spectrometer after at least one enrichment step. Polarity conditions ensure that the chemical substance(s) is (are) not retained on the chromatographic stationary phase during the whole normal analysis time, for example high polar chemical substance(s) and medium polar to low polar eluent system on reversed phase material. This results in a known signal of the chemical substance(s), which can be monitored at arbitrary point of time by the mass spectrometer, and readout of the chemical substances at any time during the analysis.

Particularly, the reagent may be identified at least to beginning of the process. The term "at least to beginning" as used herein refers to a point of time before the input of the reagent into the analysis system. To readout the chemical substance, the chemical substance is enriched upfront or upstream to the mass spectrometric detection by a specific system initialization run which is done only once after each change in the reagent part of the system. Initialization run may for example use prolonged enrichment time of several minutes, e.g., 10 min, which is much longer than usual gradient time of standard application. Thus during standard application enrichment is insufficient to allow detection and the stationary phase is cleaned during each application by a washing step. Thereby, it is possible for the enriched chemical substance to cause an identifiable background signal of the mass spectrometer.

The chemical substance may be configured to prevent retaining thereof on a stationary phase of the liquid chromatograph. Thus, it is ensured that the chemical substance follows the reagent throughout the workflow such that reagent identity is unambiguously detectable when enriched.

Particularly, polarity conditions and concentration of the chemical substance ensure that coding chemicals are not retained in sufficient concentrations on the chromatographic stationary phase during standard application. Thus, the mass spectrometer will not detect the chemical substance during normal applications.

For example, the polarity and the molecular weight of the chemical substance may be adapted to the stationary phase of the liquid chromatograph such that the chemical substance is prevented from being retained on the stationary phase of the liquid chromatograph.

The polarity of the chemical substance may be adapted by means of using a mixture of isobaric oligomers of the chemical substance. Thus, the used chemical substances show almost identical behavior during the reagent processing and chromatography as the reagent of interest. Thereby, identity of the reagents may be unambiguously detected.

The molecular weight may be adapted by using homologs, derivatives or isotope labelling of the chemical substance. Thus, the molecular weight may be adapted in a rather simple manner.

The liquid chromatograph may comprise a liquid chromatography separation station comprising a plurality of liquid chromatography channels, wherein the chemical substance is assigned to one of the plurality of liquid chromatography channels.

The term "liquid chromatograph separation station" as used herein refers to an analytical apparatus or module or a unit in an analytical apparatus designed to subject the prepared samples to chromatographic separation in order for example to separate analytes of interest from matrix components, e.g., remaining matrix components after sample preparation that may still interfere with a subsequent detection, e.g., a mass spectrometry detection, and/or in order to separate analytes of interest from each other in order to enable their individual detection. According to an embodiment, the liquid chromatograph separation station is an intermediate analytical apparatus or module or a unit in an analytical apparatus designed to prepare a sample for mass spectrometry and/or to transfer the prepared sample to a mass spectrometer. In particular, the liquid chromatograph separation station is a multi-channel liquid chromatograph separation station comprising a plurality of liquid chromatography channels.

A "liquid chromatography channel" is a fluidic line comprising at least one capillary tubing and/or liquid chromatography column comprising a stationary phase selected according to the type of sample(s) and analytes and through which a mobile phase is pumped in order to trap and/or separate and elute and/or transfer analytes of interest under selected conditions, e.g., according to their polarity or log P value, size or affinity, as generally known. The at least one liquid chromatography column in the at least one liquid chromatography channel may be exchangeable. In particular, the liquid chromatography may comprise more liquid chromatography columns than liquid chromatography channels, where a plurality of liquid chromatography columns may be interchangeably coupled to the same liquid chromatography channel. A capillary tubing may bypass a liquid chromatography column or may allow adjustment of dead volumes to fine-tune elution time windows.

The liquid chromatography separation station typically further comprises also a sufficient number of pumps, e.g., binary pumps in case of conditions requiring the use of elution gradients, and several switching valves.

Thus, by detecting the chemical substance at the mass spectrometer, it may be detected whether the reagent is associated with the correct or target channel.

Particularly, a flow of the reagent through one of the channels may be tracked. Thus, it may be detected whether the reagent flows through the correct or target channel.

The method may further comprise detecting a flow of the reagent through the channel to which the chemical substance is assigned by detecting whether an actual detection signal of the mass spectrometer includes a reagent detection signal representing the reagent and the substance detection signal. Thus, if both the reagent detection signal representing the reagent and the substance detection signal are detected, a flow of the reagent through the target channel may be detected.

The chemical substance may be assigned to one of the plurality of liquid chromatography channels depending on the type of reagent. Thus, an effective assignment of the reagent to the channels is provided.

The method may further comprise adding a composition of different chemical substances to the reagent, processing the reagent together with the composition of chemical substances by means of the analysis system, and identifying the reagent based on a detection of a substance detection signal pattern of the mass spectrometer including substance detection signals representing the composition of chemical substances. Thus, a chemical coding for the reagent is provided improving the detection quality for detecting the identity of the reagent.

The method may further comprise providing a plurality of reagents, adding a composition of different chemical substances to each of the plurality of reagents, wherein the compositions added to the plurality of reagents are different from one another, processing the plurality of reagents together with the compositions of chemical substances by means of the analysis system, and identifying each of the plurality of reagents based on a detection of substance detection signal patterns of the mass spectrometer including substance detection signals representing the different compositions of chemical substances. Thus, even a plurality of reagents which are processed in a parallel manner or at the same time may be unambiguously and reliably identified. Particularly, the provision of a composition of different chemical substances allows to provide a chemical coding of the respective reagents such that the reagents may be unambiguously identified.

The number of compositions may correspond to the number of liquid chromatography channels. Thus, to each channel a kind of signature may be assigned.

The method may further comprise adding a composition of different chemical substances to the reagent, wherein the chemical substances may differ from one another at least by the molecular weight. Thus, a signature is generated by a variable composition of defined substances, which are chemically different or stable isotopes of one chemical substance, with different molecular weight, wherein the applied concentration of each species is typically equal. The number of digital patterns, which are needed, is equal to the number of flow paths or channels which have to be differentiated. For example, five flow paths or channels need five different chemical codes provided by the compositions only.

The chemical substances may be enriched on the chromatographic column of the liquid chromatograph. Thus, the chemical substances may be enriched without additional constructional members for the liquid chromatograph. Rather, the components already present in the liquid chromatograph may be used.

The enriched chemical substances may be released from the chromatographic column and may be eluted into the mass spectrometer. Thus, when enriched, the chemical substances are transported to the mass spectrometer in order to be detected.

The chemical substance may be at least one element selected from the group consisting of: peptides, derivatives of peptides, peptide nucleic acids, oligonucleotides, carbohydrates, derivatives of carbohydrates, and oligomers. Thus, substances which may be well handled may be used.

The method may further comprise generating a code by adding at least two different chemical substances to the reagent with each chemical substance having a predetermined concentration, wherein the predetermined concentration of at least one of the chemical substances is above a detection level of the mass spectrometer. Thus, a safe code may be generated in a rather simple manner by varying the concentration of at least two different chemical substances.

The step of adding of at least one chemical substance to the reagent may be carried out in a factory made step. Thus, it is not the user of the analysis system which has to add the chemical substance to the reagent but this is done beforehand by the manufacturer of the reagent. Thereby, the identity and quality of the reagent is ensured as the reagent may not be manipulated by the user of the analysis system. Thus, the chemical coding of the reagent by the manufacturer allows to detect if the reagent has been manipulated or modified by the user of the analysis system.

The disclosure further provides and proposes a computer program including computer-executable instructions for performing the method according to the present disclosure in one or more of the embodiments enclosed herein when the program is executed on a computer or computer network. Specifically, the computer program may be stored on a computer-readable data carrier. Thus, specifically, one, more than one or even all of the method steps as indicated above may be performed by using a computer or a computer network, typically by using a computer script.

The disclosure further provides and proposes a computer program product having program code means, in order to perform the method according to the present disclosure in one or more of the embodiments enclosed herein when the program is executed on a computer or computer network. Specifically, the program code means may be stored on a computer-readable data carrier.

Further, the disclosure provides and proposes a data carrier having a data structure stored thereon, which, after loading into a computer or computer network, such as into a working memory or main memory of the computer or computer network, may execute the method according to one or more of the embodiments disclosed herein.

The disclosure further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the disclosure proposes and discloses a modulated data signal which contains instructions readable by a computer system or computer network, for performing the method according to one or more of the embodiments disclosed herein.

Typically, referring to the computer-implemented aspects of the disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present disclosure further provides:
A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer script, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Summarizing the findings of the disclosed method, the following embodiments are disclosed:

Embodiment 1: Method for identifying a reagent during a process in an analysis system, wherein the analysis system comprises a liquid chromatograph and a mass spectrometer, the method comprising:
providing a reagent,
adding at least one chemical substance to the reagent with a concentration being below a detection level of the mass spectrometer,
enriching the chemical substance within the liquid chromatograph to a higher concentration above the detection level of the mass spectrometer,
processing the reagent together with the enriched chemical substance by means of the analysis system, and
identifying the reagent based on a detection of a substance detection signal of the mass spectrometer representing the chemical substance.

Embodiment 2: Method according to embodiment 1, wherein the reagent is identified at least to beginning of the process.

Embodiment 3: Method according to embodiment 1 or 2, wherein the chemical substance is configured to prevent retaining thereof on a stationary phase of the liquid chromatograph.

Embodiment 4: Method according to embodiment 3, wherein the polarity and the molecular weight of the chemical substance are adapted to the stationary phase of the liquid chromatograph such that the chemical substance is prevented from being retained on the stationary phase of the liquid chromatograph.

Embodiment 5: Method according to embodiment 4, wherein the polarity of the chemical substance is adapted by means of using a mixture of isobaric oligomers of the chemical substance.

Embodiment 6: Method according to embodiment 3 or 4, wherein the molecular weight is adapted by using homologs, derivatives or isotope labelling of the chemical substance.

Embodiment 7: Method according to any one of embodiments 1 to 6, further comprising adding a composition of different chemical substances to the reagent, wherein the chemical substances differ from one another at least by the molecular weight.

Embodiment 8: Method according to any one of embodiments 1 to 7, wherein the chemical substance is enriched on a chromatographic column of the liquid chromatograph.

Embodiment 9: Method according to embodiment 8, wherein the enriched chemical substance is released from the chromatographic column and is eluted into the mass spectrometer.

Embodiment 10: Method according to any one of embodiments claims 1 to 9, wherein the chemical substance is at least one element selected from the group consisting of: peptides, derivatives of peptides, peptide nucleic acids, oligonucleotides, carbohydrates, derivatives of carbohydrates and oligomers.

Embodiment 11: Method according to any one of embodiments 1 to 10, further comprising generating a code by adding at least two different chemical substances to the reagent with each chemical substance having a predetermined concentration, wherein the predetermined concentration of at least one of the chemical substances is above a detection level of the mass spectrometer.

Embodiment 12: Method according to any one of embodiments 1 to 11, wherein adding of at least one chemical substance to the reagent is carried out in a factory made step.

In order that the embodiments of the present disclosure may be more readily understood, reference is made to the following examples, which are intended to illustrate the disclosure, but not limit the scope thereof.

With reference to FIG. 1, an example of an analysis system 100 is described. The analysis system may be a clinical diagnostic system. The analysis system 100 comprises at least a liquid chromatograph 102 and a mass spectrometer 104. In the present embodiment, the analysis system 100 further comprises a sample preparation station 106 for the automated pre-treatment and preparation of samples 108 each comprising at least one analyte of interest.

The liquid chromatograph 102 comprises a liquid chromatography separation station 110 comprising a plurality of liquid chromatography channels 112. The liquid chromatography channels 112 may differ from one another in that there are liquid chromatography channels 112 with a shorter cycle time and liquid chromatography channels 112 with a longer cycle time. However, the liquid chromatography separation station 110 may comprise a plurality of only faster liquid chromatography channels 112, or a plurality of only slower liquid chromatography channels 112. The analysis system 100 further comprises a sample preparation/liquid chromatography interface 114 for inputting prepared samples into any one of the liquid chromatography channels 112.

The analysis system 100 further comprises a liquid chromatography/mass spectrometer interface 116 for connecting the liquid chromatography separation station 110 to the mass spectrometer 104. The liquid chromatography/mass spectrometer interface 116 comprises an ionization source 118 and an ion mobility module 120 between the ionization source 118 and the mass spectrometer 104. The ion mobility module 120 may be a high-field asymmetric waveform ion mobility spectrometry (FAIMS) module. The mass spectrometer 104 is a tandem mass spectrometer and in particular a triple quadrupole mass spectrometer, capable of multiple reaction monitoring (MRM).

The analysis system 100 further comprises a controller 122 programmed to assign the samples 108 to pre-defined sample preparation workflows each comprising a pre-defined sequence of sample preparation steps and requiring a pre-defined time for completion depending on the analytes of interest. The controller 122 is further programmed to assign (reserve in advance) a liquid chromatography channel 112 for each prepared sample depending on the analytes of interest and to plan a liquid chromatography channel input sequence I1-$n$ for inputting the prepared samples that allows analytes of interest from different liquid chromatography channels 112 to elute in a non-overlapping LC eluate output sequence E1-$n$ based on expected elution times. The controller 122 is further programmed to set and initiate a sample preparation start sequence S1-$n$ that generates a prepared sample output sequence P1-$n$ that matches the liquid chromatography channel input sequence I1-$n$.

In FIG. 1, each sample of the sample preparation start sequence S1-$n$, each prepared sample of the prepared sample output sequence P1-$n$ and liquid chromatography channel input sequence I1-$n$, each liquid chromatography eluate of the liquid chromatography eluate output sequence E1-$n$ is indicated in a segment of a sequence comprising non-overlapping adjacent segments, each segment representing schematically one reference period. Each sequence is thus a sequence of reference periods or time units, the length of which can be fixed and remains constant across the different sequences.

Preparation of new samples in the sample preparation start sequence S1-$n$ is started with a frequency of one sample per reference period or at intervals separated by one or more reference periods, indicated by empty segments in the sequence, in which no sample preparation is started.

Also, preparation of samples in the prepared sample output sequence P1-$n$ is completed with a frequency of one prepared sample per reference period or at intervals separated by one or more reference periods, indicated by empty segments in the sequence, in which no sample preparation is completed.

Also, the prepared samples are inputted in the respective assigned liquid chromatography channels 112 according to the liquid chromatography channel input sequence I1-$n$ with a frequency of one liquid chromatography channel input per reference period or at intervals separated by one or more reference periods, indicated by empty segments in the sequence, in which no liquid chromatography channel input takes place.

Also, the liquid chromatography eluates in the liquid chromatography eluate output sequence E1-$n$ are outputted with a frequency of one liquid chromatography eluate per reference period or at intervals separated by one or more reference periods, indicated by empty segments in the sequence, in which no liquid chromatography eluate is outputted.

The liquid chromatography channels 112 are alternately connectable to the liquid chromatography/mass spectrometer interface 116 and the controller 122 controls a valve switching 124 according to the liquid chromatography eluate output sequence E1-$n$ for inputting one liquid chromatography eluate at a time into the ionization source 118. In particular, the liquid chromatography eluates in the liquid chromatography eluate output sequence E1-$n$ are inputted into the ionization source 118 with a frequency of one liquid chromatography eluate per reference period or at intervals separated by one or more reference periods according to the liquid chromatography eluate output sequence E1-$n$.

The ionization source 118 is a double ionization source, including an ESI source 126 and an APCI source 128, where depending on the liquid chromatography eluate in the liquid chromatography eluate output sequence E1-$n$ and on the analyte(s) of interest contained therein the controller 122 may select one of the two ionization sources 126, 128 that is most appropriate. When setting the sample preparation start sequence S1-$n$, the controller 122 may group together (place adjacent to each other in the sequence) samples also according to the ionization source 126, 128 so that frequent switch between ionization sources 126, 128 is prevented. Ionization source switching may be planned during one or more empty reference periods for example.

With continued reference to FIG. 1, a method for identifying a reagent 130 during a process in an analysis system 112 is described. The method comprises providing a reagent 130. The reagent 130 may be present in a reagent vessel 132 such as a container. A chemical substance 134 is added to the reagent 130 with a concentration being below a detection level of the mass spectrometer 104. The adding of the chemical substance 134 to the reagent 130 is carried out in a factory made step. The reagent container 132 may be input to the sample preparation station 106. The sample 108 is prepared using the reagent 130. For example, a predefined dose of the reagent 130 is dispensed into the sample 108. In any case, the reagent 130 together with the chemical substance 134 is added to the sample 108 before the sample 108 is input into the liquid chromatograph 102.

Then, the sample 108 is processed together with the reagent 130 and the chemical substance 134 by means of the analysis system 100. With other words, the thus prepared sample 108 together with the reagent 130 and the chemical substance 134 is input into the liquid chromatograph 102, passes through the liquid chromatograph 102 and is input into the mass spectrometer 104. Upfront or upstream the mass spectrometer 104, the chemical substance 134 is enriched to a higher concentration above the detection level of the mass spectrometer. The chemical substance 134 is enriched on a chromatographic column of the liquid chromatograph 102. Subsequently, the enriched chemical substance 134 is released from the chromatographic column and is eluted into the mass spectrometer 104.

By means of the mass spectrometer 104, a component and/or components of the sample 108 is detected and measured. In addition, the reagent 130 is detected and measured by the mass spectrometer 104. The reagent 130 is identified at least to beginning of the process. The reagent 130 is identified based on a detection of a substance detection signal of the mass spectrometer 104 including substance detection signals representing the chemical substance 134 which has been enriched beforehand. With other words, the signal of the mass spectrometer 104 not only includes the detection result corresponding to the reagent 130 but also includes signals unique to the chemical substance 134, thereby allowing to unambiguously identify the reagent 130. With this method, the reagent 130 is continuously identified during the process. Particularly, to readout the chemical substance 134 in the mass spectrometer 104, the chemical substance 134 is enriched upfront to the mass spectrometric detection by a specific system initialization run which is done only once after each change in the reagent part of the analysis system 100, i.e., when a new reagent is input. The initialization run may for example use prolonged enrichment time of several minutes, e.g., 10 min, which is much longer than usual gradient time of standard application. Thus, during standard application enrichment is insufficient to allow detection and stationary phase of the chromatographic column of the liquid chromatograph 102 is cleaned during each application by a washing step.

Hereinafter, specific details of chemical substances 134 that may be used with the disclosed method will be described. Basically, the reagent 130 comprises at least one analyte of interest and the chemical substances 134 are chemical isotopes and/or have similar polarity as the analyte of interest in order to ensure that the used chemicals show almost identical behavior during the sample and reagent processing and chromatography than the analyte of interest as they have to follow the same workflow as the analyte. The chemical substances 134 have an identical the molecular weight. The chemical substance 134 is at least one element selected from the group consisting of: peptides, derivatives of peptides, peptide nucleic acids, oligonucleotides, and oligomers. Further, the chemical substances are configured to prevent retaining thereof on a stationary phase of the liquid chromatograph 102. This may be realized in that the polarity and the molecular weight of the chemical substances 134 are adapted to the stationary phase of the liquid chromatograph 102 such that the chemical substances 134 are prevented from being retained on the stationary phase of the liquid chromatograph 102. For example, the polarity of the chemical substances 134 is adapted by means of using a mixture of isobaric oligomers or isotopes of the chemical substances 134 and the molecular weight is adapted by using homologs, derivatives or isotope labelling of the chemical substances 134. More particularly, the polarity of the chemical substances 134 is adapted by means of using a mixture of oligomers or derivatives of the chemical substances 134. Each oligomer component has a labeling group 136 for molecular weight coding which is measured intact or released during a mass spectrometric process and measured by means of the mass spectrometer 104 as will be described in further detail below.

Figure 2:
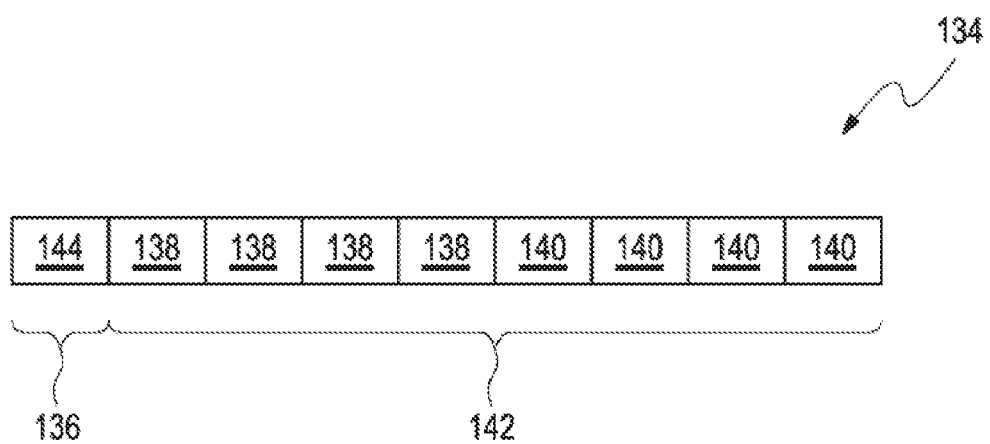
FIG. 2 shows schematically the construction a chemical substance.

FIG. 2 shows schematically the construction of one of the chemical substances 134. The chemical substances 134 comprise polar molecule groups 138 and lipophilic molecule groups 140. The chemical substances 134 are formed from monomeric blocks having a structure of $(polar)_n$-$(lipophil)_m$, wherein (polar) represents a polar molecule group 138, (lipophil) represents a lipophilic molecule group 140 and n, m are integers greater than 0. More particularly, the chemical substances are formed from monomeric building blocks n*(polar) and m*(lipophil) which are polymerized randomly, wherein (polar) represents a polar molecule group 138, (lipophil) represents a lipophilic molecule group 140 and n, m are integers greater than 0. In the example shown in FIG. 2, the chemical substance 134 comprises four polar molecule groups 138 followed by four lipophilic molecule groups 140. Thus, each chemical substance 134 comprises an isobaric oligomer group 142 and at least one molecular weight coding group 144, wherein the isobaric oligomer group 142 and the molecular weight coding group 144 of the different chemical substances 134 differ from one another.

The chemical substances 134 may thus be used for chemical coding of the samples. The number of target analytes is highly depending of the application menu on the analysis system 100. A prerequisite to the coding chemicals is therefore to cover the whole polarity range of the application menu. This is achieved by a composition of a complex functional entity of coding chemicals as described above. The monomers are designed to have identical molecular weight (isobaric building blocks), thus the overall molecular weight of this oligomeric subunit is constant independently of the ratio n/m generating an isobaric oligomer backbone. The sequence distribution of n and m may be random or not random depending on the desired readout of the mass spectrometer 104, molecular weight only by using selected ion monitoring or by readout of molecular weight and sequence by fragmentation pattern (daughter ion scan). Attached to this building block there is a molecular weight discriminating label. Function of the molecular weight coding group 144 is to enable the generation of a variety of encoding substances with different molecular weight. This is generated for example by using different amounts of stable isotopic labels or different chemical functionality within the molecular weight coding group 144. Function of the oligomeric building block is to generate a polarity leader in which the subunits have different chromatographic properties (logP) but have identically molecular weights. Thus, by the combination of the molecular weight coding group 144 and the isobaric oligomer backbone it is possible to generate a chemical coding-entity. Examples for monomers used for generation of the isobaric oligomer backbone are serinpropylether having a molecular weight of 129.16, homoserin-ethylether having a molecular weight of 129.16, and glutamine acid having a molecular weight of 129.11.

Thus, finally each molecular weight coding group 144 is linked to a mixture of an isobaric oligomer backbone which covers the whole chromatographic space of the application. Thus, independently of the polarity (logP) of the analytes of interest at least on member of each chemical coding entity or chemical substance 134 will be detected by the mass spectrometer 104 in the same time window as the analyte of interest. For example, by using 7 different molecular weight coding group 144 attached to the same isobaric oligomer backbone it is possible to generate a matrix of 107 different chemical codes. In this case, the only differentiation criterion is the molecular weight (SIM readout only).

As described above, the liquid chromatography separation station 110 comprises a plurality of liquid chromatography channels 112. Thus, a plurality of samples 108 and reagents 130 may be processed at the same time. The chemical substance 134 is assigned to one of the plurality of liquid chromatography channels 112. For example, the chemical substance 134 is assigned to one of the plurality of liquid chromatography channels 112 depending on the type of reagent 130. Thereby, a flow of the reagent 130 through one of the channels 112 may be tracked when the chemical substance 134 is enriched. Particularly, a flow of the reagent 130 through the channel 112 to which the chemical substance 134 is assigned may be detected by detecting whether an actual detection signal of the mass spectrometer 104 includes a reagent detection signal representing the reagent 134 and the substance detection signal. With other words, it may be detected whether the reagent 130 has passed the target or correct channel 112.

The method may further comprise providing a plurality of reagents 130, adding a composition 146 of different chemical substances 134 to each of the plurality of reagents 130, wherein the compositions 146 added to the plurality of samples 108 are different from one another, processing the plurality of reagents 130 together with the compositions 146 of chemical substances 134 by means of the analysis system 100, and identifying each of the plurality of reagents 130 based on a detection of substance detection signal patterns of the mass spectrometer 104 including substance detection signals representing the different compositions 146 of chemical substances 134. The chemical substances 134 differ from one another at least by the molecular weight. In this case, the number of compositions 146 may correspond to the number of liquid chromatography channels 112. Thus, a code may be generated by adding at least two different chemical substances 134 to the reagent 130. For this purpose, each chemical substance 134 has a predetermined concentration, wherein the predetermined concentration of at least one of the chemical substances 134 is above a detection level of the mass spectrometer 104.

LIST OF REFERENCE NUMBERS

- 100 analysis system
- 102 liquid chromatograph
- 104 mass spectrometer
- 106 sample preparation station
- 108 sample
- 110 liquid chromatography separation station
- 112 liquid chromatography channel
- 114 sample preparation/liquid chromatography interface
- 116 liquid chromatography/mass spectrometer interface
- 118 ionization source
- 120 ion mobility module
- 122 controller
- 124 valve switching
- 126 ESI source
- 128 APCI source
- 130 composition
- 134 chemical substance
- 136 labeling group
- 138 polar molecule groups
- 140 lipophilic molecule group
- 142 isobaric oligomer group
- 144 molecular weight coding group
- 146 composition

What is claimed is:

1. A method for identifying a solvent lot during a process in an analysis system, wherein the analysis system comprises a liquid chromatograph and a mass spectrometer, the method comprising:
   providing a solvent from a lot,
   adding at least one chemical substance to the solvent lot, wherein the chemical substance is at a concentration being below a detection level of the mass spectrometer,
   enriching the chemical substance within the liquid chromatograph during processing of the solvent lot to a concentration detectable by the mass spectrometer,
   processing the solvent lot associated with the enriched chemical substance with the analysis system, and
   identifying the solvent lot based on a detection of a substance detection signal of the mass spectrometer representing the chemical substance, wherein the solvent lot is continuously identified by the chemical substance during the process to detect whether the specific solvent lot has passed a target or a correct liquid chromatography channel of the liquid chromatograph.

2. The method according to claim 1, wherein the chemical substance is configured to prevent retaining thereof on a stationary phase of the liquid chromatograph.

3. The method according to claim 2, wherein the polarity and the molecular weight of the chemical substance are adapted to the stationary phase of the liquid chromatograph such that the chemical substance is prevented from being retained on the stationary phase of the liquid chromatograph.

4. The method according to claim 3, wherein the polarity of the chemical substance is adapted by using a mixture of isobaric oligomers of the chemical substance.

5. The method according to claim 2, wherein the molecular weight is adapted by using homologs, derivatives or isotope labelling of the chemical substance.

6. The method according to claim 1, further comprising adding a composition of different chemical substances to the solvent lot, wherein the chemical substances differ from one another at least by the molecular weight.

7. The method according to claim 1, wherein the chemical substance is enriched on a chromatographic column of the liquid chromatograph.

8. The method according to claim 1, wherein the enriched chemical substance is released from the chromatographic column and is eluted into the mass spectrometer.

9. The method according to claim 1, wherein the chemical substance is at least one element selected from the group consisting of: peptides, derivatives of peptides, peptide nucleic acids, oligonucleotides, carbohydrates, derivatives of carbohydrates, and oligomers.

10. The method according to claim 1, further comprising generating a code by adding at least two different chemical substances to the solvent lot with each chemical substance having a predetermined concentration, wherein the predetermined concentration of at least one of the chemical substances is detectable by the mass spectrometer.

11. The method according to claim 1, wherein adding of at least one chemical substance to the solvent lot is carried out in a factory made step.

12. The method according to claim 1, wherein the solvent lot comprises a reactant selected from the group consisting of enzymes, enzyme substances, conjugated dyes, protein-binding molecules, ligands, nucleic acid binding molecules, antibodies, chelating agents, promoters, inhibitors, epitopes, and antigens.

13. The method according to claim 1, wherein the chemical substance has a similar polarity as the solvent lot.

14. The method according to claim 1, wherein the chemical substance is selected from the group consisting of peptides, peptide nucleic acids, oligonucleotides, carbohydrates and derivatives thereof, and oligonucleotides.

* * * * *